(12) United States Patent
Nair et al.

(10) Patent No.: US 9,029,617 B2
(45) Date of Patent: May 12, 2015

(54) PROCESS FOR 1-CHLORO-3,3,3-TRIFLUOROPROPENE FROM TRIFLUOROPROPENE

(71) Applicant: Honeywell International Inc., Morristown, NJ (US)

(72) Inventors: Haridasan K. Nair, Williamsville, NY (US); David Nalewajek, West Seneca, NY (US); Andrew Joseph Poss, Kenmore, NY (US); Yian Zhai, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/330,744

(22) Filed: Jul. 14, 2014

(65) Prior Publication Data

US 2015/0045590 A1  Feb. 12, 2015

Related U.S. Application Data

(60) Provisional application No. 61/863,735, filed on Aug. 8, 2013.

(51) Int. Cl.
   C07C 17/25    (2006.01)
   C07C 17/04    (2006.01)
   C07C 17/10    (2006.01)
   C07C 17/156   (2006.01)
   C07C 17/354   (2006.01)

(52) U.S. Cl.
   CPC ............... C07C 17/25 (2013.01); C07C 17/04 (2013.01); C07C 17/10 (2013.01); C07C 17/156 (2013.01); C07C 17/354 (2013.01)

(58) Field of Classification Search
   CPC ...... C07C 17/25; C07C 17/354; C07C 17/10; C07C 17/156; C07C 17/04
   USPC ................................... 570/153, 156
   See application file for complete search history.

(56) References Cited

U.S. PATENT DOCUMENTS

| | | | |
|---|---|---|---|
| 8,388,857 B2 | 3/2013 | Elsheikh et al. | |
| 8,404,907 B2 | 3/2013 | Nair et al. | |
| 8,450,537 B2 | 5/2013 | Rao et al. | |
| 8,536,388 B2 * | 9/2013 | Smith et al. | 570/158 |
| 8,633,340 B2 * | 1/2014 | Smith et al. | 570/169 |
| 8,877,086 B2 * | 11/2014 | Mahler et al. | 252/67 |
| 2005/0033097 A1 | 2/2005 | Tung et al. | |
| 2009/0270661 A1 | 10/2009 | Tung et al. | |
| 2011/0083955 A1 | 4/2011 | Tirtowidjojo et al. | |
| 2011/0201853 A1 | 8/2011 | Tung et al. | |
| 2011/0218370 A1 | 9/2011 | Elsheikh et al. | |
| 2011/0269861 A1 | 11/2011 | Johnson et al. | |
| 2012/0043492 A1 | 2/2012 | Williams et al. | |
| 2012/0271069 A1 | 10/2012 | Wang et al. | |
| 2013/0150633 A1 | 6/2013 | Zhai et al. | |

FOREIGN PATENT DOCUMENTS

WO    2013085765 A1    6/2013

* cited by examiner

*Primary Examiner* — Shailendra Kumar
(74) *Attorney, Agent, or Firm* — Erika Wilson

(57) ABSTRACT

The present invention provides routes for making 1-chloro-3,3,3-trifluoropropene (HCFO-1233zd) from commercially available raw materials. More specifically, this invention provides several routes for forming HCFO-1233zd from 3,3,3-trifluoropropene (FC-1234zf).

21 Claims, No Drawings

PROCESS FOR 1-CHLORO-3,3,3-TRIFLUOROPROPENE FROM TRIFLUOROPROPENE

CROSS-REFERENCE TO RELATED APPLICATION

This application claims domestic priority from commonly owned U.S. Provisional Application Ser. No. 61/863,735 filed 8 Aug. 2013, the disclosure of which is hereby incorporated herein by reference.

FIELD OF THE INVENTION

The present invention provides routes for making 1-chloro-3,3,3-trifluoropropene (HCFO-1233zd) from commercially available raw materials. More specifically, this invention provides routes for HCFO-1233zd from commercially available 3,3,3-trifluoropropene (FC-1234zf).

BACKGROUND OF THE INVENTION

Trans 1-chloro-3,3,3-trifluoropropene (HCFO-1233zd) can be used for many applications including use as a refrigerant, blowing agent, solvent, cleaning agent and monomer for polymer compounds. The compounds of the present invention are part of a continued search for the next generation low global warming potential materials with low environmental impact.

Many methods are known in the art for making HCFO-1233zd (trans), most of them using three carbon starting materials which are obtained via multiple steps. For example, U.S. Pat. Nos. 5,777,184 and 6,472,573 describe the preparation of $CF_3CH=CHCl$ from $CCl_3CH_2CHCl_2$ (240fa) with HF in the presence of a catalyst. Treatment of $CF_3CH_2CF_2H$ (245fa) and HCl at 280° C. with chromium catalyst is reported to give 1233zd (trans and cis), see EP 2327680. Reaction of $CF_3CH=CH_2$ with chlorine and HF affords 1233zd as one of the products; see WO 2008/54782 A1.

All of the above processes involve three carbon starting materials which in turn are made in multiple steps and thus there is a need to develop cost effective routes which utilize commercially available raw materials. The present invention addresses this issue by utilizing 3,3,3-trifluoropropene (FC-1234zf).

SUMMARY OF THE INVENTION

The present invention describes the preparation of HCFO-1233zd from commercially available 3,3,3-trifluoropropene (FC-1234zf). The compound 3,3,3-tri-fluoropropene can be purchased from a number of vendors or it can be easily prepared via well-known synthetic routes.

The compound 3,3,3-trifluoropropene can be converted to $CF_3CH=CHCl$ via three different routes, as follows:

First Route:
In a first method, $CF_3CH=CH_2$ is converted directly to HCFO-1233zd in a single step via oxychlorination with HCl, $O_2$ and a supported $CuCl_2$ catalyst.

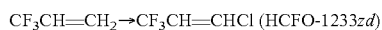

Modifications of the oxychlorination reaction using copper chloride, other copper salts, with rare earth salts or halides can be made to optimize the reaction. See, J. Chem. Education, 1986, 63, 1056-1058 and U.S. Pat. No. 4,025,461.

Reaction conditions, especially the temperature of the reaction, can be adjusted to provide the desired chlorine substituted rather than the unwanted addition product. Typically, the reaction is done by passing a vapor mixture of the olefin, oxygen and HCl over a supported copper catalyst at an elevated temperature, e.g., from 400° to 500° C. as shown in Equation (1) below:

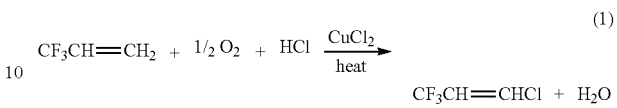

Second Route:
In a second method, 3,3,3-trifluoropropene is reacted with XCl (X=Br, I, OR), such that X is added across the double to afford $CF_3CHXCH_2Cl$ which is then converted to $CF_3CH=CHCl$ via elimination of HX, as shown below in Equation (2):

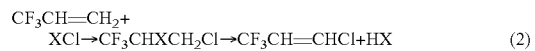

The by-product formed is $CF_3CHClCH_2X$ which can be recycled as starting material after dechlorinating with Zn as shown below:

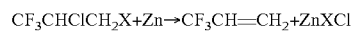

Third Route:
A third method involves addition of hydrogen to 3,3,3-trifluoropropene to afford $CF_3CH_2CH_3$, which is then chlorinated and dehydrochlorinated to give 1-chloro-3,3,3-trifluoropropene (HCFO-1233zd) as depicted below in Equations (3), (4) and (5):

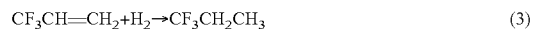

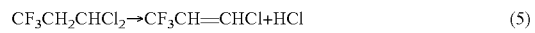

In the reaction of Equation (4), $CF_3CH_2CCl_3$ can also be produced at times which can be converted to 1233zd as shown below:

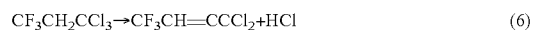

The process involves dehydrochlorination, hydrogenation and subsequent elimination of HCl as depicted in Equations (6), (7), and (8), respectively.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

The present invention provides routes for making 1-chloro-3,3,3-trifluoropropene (HCFO-1233zd) from commercially available raw materials. More specifically, this invention provides several routes for forming HCFO-1233zd from 3,3,3-trifluoropropene (FC-1234zf).

Accordingly, one embodiment of the invention is directed to a process for the formation of 1-chloro-3,3,3-trifluoropropene from 3,3,3-trifluoropropene (FC-1234zf), selected from the group of reactions consisting of:

(a) the direct conversion of 3,3,3-trifluoropropene into $CF_3CH=CHCl$ via an oxychlorination reaction;

(b) the reaction of 3,3,3-trifluoropropene with XCl (wherein X=Br, I, OR), whereby X is added across the double to afford $CF_3CHXCH_2Cl$ which is then converted to $CF_3CH=CHCl$ by an HX elimination reaction;

(c) the reaction of 3,3,3-trifluoropropene with hydrogen to afford $CF_3CH_2CH_3$, which is then chlorinated and dehydrochlorinated to give 1-chloro-3,3,3-trifluoropropene; and (d) combinations of two or more of these reactions.

In certain embodiments, the oxychlorination reaction comprises the reaction of oxygen and hydrogen chloride with the propene, in the vapor phase over a supported catalyst.

In certain embodiments, the supported catalyst is selected from the group consisting of copper chloride salts, rare earth salts, and equivalents thereof.

In certain embodiments, the catalyst comprises $CuCl_2$.

In certain embodiments, the catalyst comprises $CuCO_3/CeO_2$.

In certain embodiments, the support of the catalyst is selected from the group consisting of carbon, alumina, and equivalents thereof.

In certain embodiments, the reaction temperature of the oxychlorination reaction ranges from 400° to 550° C.

In certain embodiments, the group X in XCl, is selected from the group consisting of Br, I, and OR, wherein R is a $C_1$ to $C_6$ carbon group.

In certain embodiments, the R group in OR, is selected from methyl, ethyl, propyl, butyl, heptyl, and hexyl.

In certain embodiments, XCl comprises BrCl.

In certain embodiments, XCl comprises ICl.

In certain embodiments, XCl comprises ROCl.

In certain embodiments, $CF_3CHXCH_2Cl$ comprises $CF_3CHICH_2Cl$.

In certain embodiments, the chlorination reaction of $CF_3CH_2CH_3$ generates a product intermediate comprising $CF_3CH_2CHCl_2$.

In certain embodiments, the dehydrochlorination reaction of $CF_3CH_2CHCl_2$ is conducted in the vapor phase at about 400° C. to yield HCFO-1233zd.

In certain embodiments, the ratio of trans to cis HCFO-1233zd is 90:10.

Another embodiment of the invention is directed to a method for producing 1-chloro-3,3,3-trifluoropropene (HCFO-1233zd) from 3,3,3-trifluoropropene (FC-1234zf) comprising the step of:

(a) directly converting FC-1234zf directly into HCFO-1233zd by passing a mixture of FC-1234zf, oxygen and hydrogen chloride over an oxychlorination catalyst at a time and temperature sufficient for the conversion.

In certain embodiments, the catalyst is selected from the group consisting of copper chloride salts, rare earth salts, and equivalents thereof.

In certain embodiments, the catalyst comprises $CuCl_2$.

In certain embodiments, the catalyst comprises $CuCO_3/CeO_2$.

In certain embodiments, the catalyst comprises a supported catalyst and the support is selected from the group consisting of carbon, alumina, and equivalents thereof.

In certain embodiments, the reaction temperature of the oxychlorination reaction ranges from 400° to 550° C.

Yet another embodiment of the invention is directed to a process for producing 1-chloro-3,3,3-trilfuoroproene (HCFO-1233zd) from 3,3,3-tri-fluoropropene (FC-1234zf) comprising the steps of:

(a) addition of XCl to 3,3,3-trifluorpropene to form $CF_3CHXCH_2Cl$; and (b) elimination of HX from $CF_3CHXCH_2Cl$ to form HCFO-1233zd.

In certain embodiments, the X group in XCl is selected from the group consisting of Br, I, and OR, wherein R is a $C_1$ to $C_6$ carbon group.

In certain embodiments, the R group in ROCl is selected from methyl, ethyl, propyl, butyl, heptyl, and hexyl.

In certain embodiments, XCl comprises BrCl.

In certain embodiments, XCl comprises ICl.

In certain embodiments, XCl comprises ROCl.

In certain embodiments, $CF_3CHXCH_2Cl$ comprises $CF_3CHICH_2Cl$.

In certain embodiments, the chlorination reaction of $CF_3CH_2CH_3$ generates a product intermediate comprising $CF_3CH_2CHCl_2$.

In certain embodiments, the dehydrochlorination reaction of $CF_3CH_2CHCl_2$ is conducted in the vapor phase at about 400° C. to yield HCFO-1233zd.

In certain embodiments, the ratio of trans to cis HCFO-1233zd is 90:10.

Yet another embodiment of the invention is directed to a process for producing 1-chloro-3,3,3-trilfuoroproene (HCFO-1233zd) from 3,3,3-trifluoropropene (FC-1234zf) comprising the steps of:

(a) hydrogenation of 3,3,3-trifluorpropene to form $CF_3CH_2CH_3$;

(b) chlorination of $CF_3CH_2CH_3$ to form $CF_3CH_2CHCl_2$ and (c) dehydrochlorination of $CF_3CH_2CHCl_2$ to form HCFO-1233zd.

In general, it is possible that certain reactions employed herein can be carried out in the liquid phase or in the gas phase, or in a combination of gas and liquid phases, and it is contemplated that the reactions can be carried out batch wise, continuously, or by a combination of these.

Preferably the reactor vessel is comprised of materials which are resistant to corrosion as Hastelloy, Inconel, Monel and/or fluoropolymers linings.

In certain embodiments the reactor vessel contains catalyst, for example a fixed or fluid catalyst bed, packed with a suitable catalyst, with suitable means to ensure that the reaction mixture is maintained with the desired reaction temperature range.

In general it is also contemplated that a wide variety of reaction pressures may be used for the reactions, depending again on relevant factors such as the specific catalyst being used. The reaction pressure can be, for example, superatmospheric, atmospheric or under vacuum and in certain preferred embodiments is from about 1 to about 200 psia, and in certain embodiments from about 1 to about 120 psia.

In certain embodiments, an inert diluent gas, such as nitrogen, may be used in combination with the other reactor feed(s).

It is contemplated that the amount of catalyst use will vary depending on the particular parameters present in each embodiment.

EXAMPLES

The following examples provide additional details regarding various embodiments of the present invention. However, the present invention is not limited to the following examples.

Example 1

Conversion of $CF_3CH=CH_2$ Directly to $CF_3CH=CHCl$ Via Oxychlorination

Into an Inconel tube reactor (0.5 inch×14 inch) was loaded 25 cc of copper chloride supported on alumina (7 to 10 g $CuCl_2$/100 g of impregnated support). Then a mixture of 3,3,3-trifluoropropene, oxygen and hydrogen chloride in the ratio 1:0.5:2, respectively, was passed over the heated supported catalyst with a contact time of from 5 to 20 sec in the temperature range of from 450° to 550° C. The yield of $CF_3CH=CHCl$ ranged from 20% to 50%. The main by-product was $CF_3CHClCH_2Cl$.

Example 2

The reaction was conducted in the same way as described in Example 1 except the catalyst used was $CuCO_3/CeO_2$ (equimolar; 7 to 10 g/100 g gamma alumina support) calcined at 900° C. for 1 hour. The conversion of $CF_3CH=CH_2$ ranged from 50% to 75% with 30% to 60% yield of $CF_3CH=CHCl$ in the product mixture for 3 runs at 450°, 500°, 550° C., respectively. Note that this reaction can be conducted in a continuous manner.

Example 3

Preparation of $CF_3CHICH_2Cl$

Into a 250 mL stainless steel autoclave containing 0.05 mol of ICl and 100 mL dichloromethane at −20° C. was condensed/added 0.05 mol of 3,3,3-trifluoropropene. The autoclave was then brought to 0° C. and stirred for 48 h. The product was washed with 5% aq. $NaHSO_3$ solution and then by water (2×25 mL) to afford the product $CF_3CHICH_2Cl$ (40%) along with $CF_3CHClCH_2I$; $CF_3CHICH_2Cl$ was separated via distillation and used for the next step.

Example 4

Conversion of $CF_3CHICH_2Cl$ to $CF_3CH=CHCl$

A stainless steel tube reactor (0.5 inch×12 inch) was loaded with 30 cc of fluorinated chromia ($Cr_2O_3$) catalyst and heated to 200° C. with a nitrogen purge. Then the nitrogen flow was stopped and $CF_3CHICH_2Cl$ was added (1 to 2 mL/min), vaporized and passed over the heated catalyst to afford a mixture of $CF_3CH=CHCl$ (60%) and $CF_3CCl=CH_2$ (40%). The $CF_3CH=CHCl$ thus formed was separated via distillation.

Example 5

Preparation of $CF_3CH=CHCl$ Via Hydrogenation, Chlorination and Dehydrochlorination of $CF_3CH=CH_2$ Step A—Hydrogenation:

Into a 350 mL stainless steel autoclave was added 1 g of hydrogenation catalyst (about 2% Pd on C), and 50 mL methanol under a nitrogen purge. The autoclave was sealed, cooled to −20° C. and evacuated to remove excess nitrogen. Next was added 0.10 mol of $CF_3CH=CH_2$. Then autoclave was brought to about 0° C. and slowly charged with 0.01 mol $H_2$; the reaction was monitored by the drop in pressure over time. The reaction was stopped once there was no more change in pressure and the product, mainly $CF_3CH_2CH_3$, was distilled off from the reactor to afford (0.08 mol, 80% yield).

Step B—Chlorination:

Chlorination of $CF_3CH_2CH_3$ to $CF_3CH_2CHCl_2$ was accomplished by passing a mixture of $CF_3CH_2CH_3$ and $Cl_2$ (about 1:2 ratio) through a heated (375° to 425° C.) tube reactor containing activated carbon. The conditions could be optimized to give mainly $CF_3CH_2CHCl_2$. The by-products formed were $CF_3CH_2CCl_3$ and $CF_3CH_2CH_2Cl$.

Step C—Dehydrochlorination of $CF_3CH_2CHCl_2$:

Vaporized $CF_3CH_2CHCl_2$ (about 30 sccm) was passed over a heated fluorinated $Cr_2O_3$ catalyst column (25 cc) in a stainless steel tube reactor (0.5 inch×14 inch) placed in a furnace (400° C.); the contact time was about 25 to 30 sec. Under these conditions 80% product in the exit stream was $CF_3CH=CHCl$ (90% trans and 10% cis). In this manner 1-chloro-3,3,3-trifluoropropene (HCFO-1233zd) could be prepared continuously.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for the formation of 1-chloro-3,3,3-trifluoropropene (HCFO-1233zd) from 3,3,3-trifluoropropene (FC-1234zf) comprising the direct conversion of 3,3,3-trifluoropropene into $CF_3CH=CHCl$ by reaction with oxygen and hydrogen chloride.

2. The method of claim 1, wherein the reaction is run in a continuous manner.

3. A method for the formation of 1-chloro-3,3,3-trifluoropropene (HCFO-1233zd) from 3,3,3-trifluoropropene (FC-1234zf), selected from the group of reactions consisting of:
(a) the reaction of 3,3,3-trifluoropropene with XCl, whereby XCl is added across the double to afford $CF_3CHXCH_2Cl$ which is then converted to $CF_3CH=CHCl$ by an HX elimination reaction;
(b) the reaction of 3,3,3-trifluoropropene with hydrogen to afford $CF_3CH_2CH_3$, which is then chlorinated and dehydrochlorinated to give 1-chloro-3,3,3-trifluoropropene; and
(c) combinations of these reactions.

4. The method of claim 3, wherein the oxychlorination reaction comprises the reaction of oxygen and hydrogen chloride with the propene, in the vapor phase over a supported catalyst.

5. The method of claim 4 where oxygen to hydrogen chloride ratio is 0.5 to 1.

6. The method of claim 4, wherein the supported catalyst is selected from the group consisting of copper chloride salts, rare earth salts, and equivalents thereof.

7. The method of claim 5, wherein the catalyst comprises $CuCl_2$.

8. The method of claim 5, wherein the catalyst comprises $CuCO_3/CeO_2$.

9. The method of claim 4, wherein the support of the catalyst is selected from the group consisting of carbon, alumina, and equivalents thereof.

10. The method of claim 4, wherein the reaction temperature of the oxychlorination reaction ranges from 400° to 550° C.

11. The method of claim 3, wherein X in XCl is selected from the group consisting of Br, I, and OR, wherein R is a $C_1$ to $C_6$ carbon group.

12. The method of claim 11, wherein R is selected from methyl, ethyl, propyl, butyl, heptyl, and hexyl.

13. The method of claim 11, wherein XCl comprises BrCl.

14. The method of claim 11, wherein XCl comprises ICl.

15. The method of claim 11, wherein XCl comprises ROCl.

16. The method of claim 11, wherein $CF_3CHXCH_2Cl$ comprises $CF_3CHICH_2Cl$.

17. The method of claim 3, wherein the chlorination reaction of $CF_3CH_2CH_3$ generates a product intermediate comprising $CF_3CH_2CHCl_2$.

18. The method of claim 17, wherein dehydrochlorination reaction of $CF_3CH_2CHCl_2$ is conducted in the vapor phase at about 400° C. to yield HCFO-1233zd.

19. The method of claim 18, wherein the ratio of trans to cis HCFO-1233zd is 90:10.

20. A process for producing 1-chloro-3,3,3-trilfuoroproene (HCFO-1233zd) from 3,3,3-tri-fluoropropene (FC-1234zf) comprising the steps of:
(a) addition of XCl to 3,3,3-trifluorpropene to form $CF_3CHXCH_2Cl$; and
(b) elimination of HX from $CF_3CHXCH_2Cl$ to form HCFO-1233zd.

21. A process for producing 1-chloro-3,3,3-trilfuoroproene (HCFO-1233zd) from 3,3,3-trifluoropropene (FC-1234zf) comprising the steps of:
(a) hydrogenation of 3,3,3-trifluorpropene to form $CF_3CH_2CH_3$;
(b) chlorination of $CF_3CH_2CH_3$ to form $CF_3CH_2CHCl_2$ and
(c) dehydrochlorination of $CF_3CH_2CHCl_2$ to form HCFO-1233zd.

* * * * *